United States Patent [19]

Pansegrau et al.

[11] Patent Number: 5,840,997
[45] Date of Patent: Nov. 24, 1998

[54] METHOD FOR THE PRODUCTION OF ALKOXY- AND ARYLOXY-PHENOLS

[75] Inventors: Paul D. Pansegrau; Brant P. Munson, both of Beulah, N. Dak.

[73] Assignee: Dakota Gasification Company, Beulah, N. Dak.

[21] Appl. No.: 831,474

[22] Filed: Mar. 31, 1997

[51] Int. Cl.$^6$ .................................................. C07C 43/16
[52] U.S. Cl. ........................... 568/648; 568/651; 568/803
[58] Field of Search ..................................... 568/648, 651, 568/803

[56] References Cited

U.S. PATENT DOCUMENTS 3,927,123  12/1975  Bourdin et al. ...................... 260/621 G

OTHER PUBLICATIONS

Profft et al; J. Prakt. Chemie. vol. 11, pp. 94–107, 1960.

*Primary Examiner*—Gary Geist
*Assistant Examiner*—Sheeni Padmanabhan
*Attorney, Agent, or Firm*—Alix, Yale & Ristas, LLP

[57] ABSTRACT

Alkoxybenzaldehydes and aryloxybenzaldehydes are converted to the corresponding phenols by reacting the benzaldehydes in an organic solvent phase with formic acid and hydrogen peroxide in an aqueous solvent phase to produce the corresponding formate ester. The formate ester is then saponified to produce the corresponding phenol.

6 Claims, No Drawings

METHOD FOR THE PRODUCTION OF ALKOXY- AND ARYLOXY-PHENOLS

FIELD OF THE INVENTION

The present invention relates to a novel combination of reagents for reaction with an alkoxybenzaldehyde or aryloxybenzaldehyde which forms an alkoxy- or aryloxy- phenol formate ester. Mild saponification of the formate ester results in production of an alkoxy- or aryloxy-phenol.

BACKGROUND OF THE INVENTION

Historically, the conversion of benzaldehydes to phenols generally follows a scheme wherein a two step process is employed. In the first step, the benzaldehyde is converted to a phenol-formate ester. In the second step, the formate ester is hydrolyzed to release the phenol. In some instances, the first step may be transparent in that the formate is never observed as a consequence of the reaction conditions employed.

The practice of such a scheme requires the use of reagent chemicals such as peracids. Specifically, peracids which have enjoyed widespread use are peracetic acid, perbenzoic acid, m-chloroperbenzoic acid and performic acid. The use of performic acid has been restricted to the utilization of formic acid as a solvent and adding an appropriate amount of hydrogen peroxide to achieve the desired oxidation. Other methods utilize highly toxic compounds, such as benzeneseleninic acid or potassium fluoride to catalyze the desired reaction, or reagents such as sodium perborate which releases boric acid in an aqueous waste stream.

Additionally, with the use of inexpensive hydrogen peroxide, a serious competing side-reaction is the undesired oxidation of the benzaldehyde to the corresponding benzoic acid. In special instances these problems have been overcome, such as a case wherein the benzaldehyde contains an ortho-hydroxyl group. This is termed a Dakin Reaction. The Dakin Reaction requires the action of hydrogen peroxide upon such a benzaldehyde under basic conditions. An expensive alternative is sodium percarbonate which is commercially available. Reaction of salicylaldehyde under such conditions results in the formation of catechol.

Under acidic conditions, the production of phenolic compounds has been restricted to the use of acetophenones rather than benzaldehydes. The conversion of acetophenones, and corresponding homologues, to phenols is termed the Baeyer-Villiger Reaction. Only one instance is known wherein a benzaldehyde is converted to a phenol under acid conditions and that was achieved by the use of potassium bisulfate to catalyze the conversion of a dialkoxybenzaldehyde to a phenol.

Attempts to convert benzaldehydes to phenols utilizing inexpensive reagents have recently been described. Some efforts have utilized a metal catalyst and either air or oxygen as the oxidant. A major drawback for these methods is that a sacrificial aldehyde is required to drive the conversion of benzaldehyde to formate ester. Other reactions which have previously been described include the conversion of bromopiperonal to bromosesamol and the conversion of piperonal to sesamol.

Still other processes for the production of alkoxyphenols have been proposed such as the mono-alkylation of catechol, or similar dihydrics, and the oxidation of anisole, or similar aryl-alkyl ethers. These two methods are nonspecific and two or more isomeric products may be formed as a consequence of the reaction. For example, treatment of catechol with dimethylsulfate under basic conditions results in formation of veratrole, as well as the desired guaiacol. Similarly, oxidation of anisole with hydrogen peroxide, with catalysis, results in the formation of guaiacol as well as 4-methoxyphenol. In both instances, separation of the undesired by-product is required, and in homologous cases this may not be trivial.

SUMMARY OF THE INVENTION

In accordance with the present invention, a method is provided for the conversion of alkoxybenzaldehydes and aryloxybenzaldehydes to alkoxyphenols and aryloxyphenols respectively. Specifically, the invention relates to the reaction of the alkoxy- or aryloxy-benzaldehydes in an organic solvent phase with hydrogen peroxide and formic acid in an aqueous solvent phase to form the corresponding formate ester which is then converted to the corresponding alkoxy- or aryloxy-phenol by saponification.

DESCRIPTION OF THE PREFERRED EMBODIMENTS

As stated, the present invention relates to the production of either alkoxy- or aryloxy-phenols. In order to simplify the description, the invention will now be described with specific reference to alkoxy-materials, but it is to be understood that the invention applies equally as well to the aryloxy-materials.

The term "alkyl" as employed herein includes both straight chain and branched chain radicals of up to 18 carbons, preferably 1 to 4 carbons, such as methyl, ethyl, propyl, isopropyl, butyl, isobutyl, sec-butyl and tert-butyl, and the like, as well as groups including 1, 2 or 3 substituents such as halo, alkenyl, alkynyl, aryl, alkyl-aryl, halo-aryl, cycloalkyl and alkylcycloalkyl.

The term "aryl" as employed herein refers to monocyclic or bicyclic aromatic groups containing 6 to 10 carbons in the ring portion, such as phenyl or naphthyl. Aryl, phenyl or naphthyl may include substituted aryl, substituted phenyl, or substituted naphthyl, which may include 1 or 2 substituents on either the phenyl or naphthyl such as alkyl, trifluoromethyl, halogen (Cl, Br, I or F), alkylsulfonyl, and/or arylsulfonyl.

The present invention involves a method for the mild conversion of an alkoxybenzaldehyde to an alkoxyphenol formate ester utilizing a combination of inexpensive reagent chemicals. Subsequent saponification of the formate ester releases the alkoxyplenol, which is isolated in a substantially pure state utilizing acid-base extraction techniques.

The following is the reaction scheme of the present invention:

Reaction Scheme

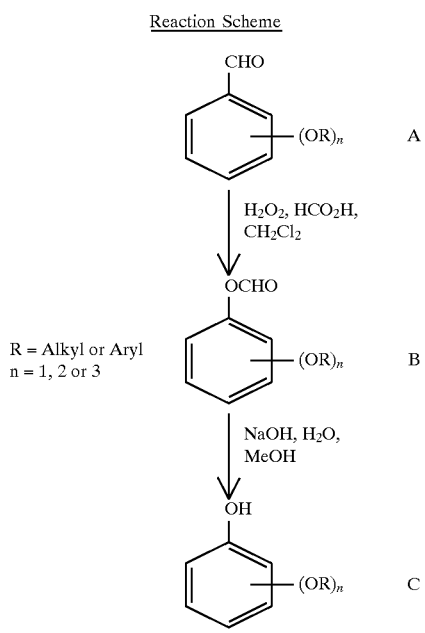

R = Alkyl or Aryl
n = 1, 2 or 3

As shown in the Reaction Scheme, the alkoxybenzaldehyde (A) in an inert solvent undergoes an oxygen insertion reaction, similar to either a Baeyer-Villiger or Dakin Reaction, by treatment with hydrogen peroxide and formic acid. The amount of hydrogen peroxide used may vary between 2 and 6 molar equivalents, preferably, 3 to 5. The amount of formic acid used may vary between 3 and 7 molar equivalents, preferably 4 to 6. The inert solvent is one which is immiscible with water, is capable of solubilizing the alkoxybenzaldehyde and performic acid and is non-reactive with both hydrogen peroxide and performic acid. The preferred inert solvents are chlorinated solvents such as dichloromethane (methylene chloride), chloroform, carbon tetrachloride, and dichloroethane. However, other solvents can be used such as ethyl acetate, butyl acetate, isobutyl acetate, propyl acetate, isopropyl acetate, pentane, hexane, heptane.

Performic acid is widely known to be an excellent oxidizing agent for a wide variety of functional groups common to organic chemistry. Performic acid is not commercially available, and therefore must be generated from formic acid and a strong oxidizing agent. The performic acid thus generated must be used immediately or it decomposes. The reason for this is probably that the performic acid either rearranges to carbonic acid, or oxidizes formic acid to carbonic acid. The carbonic acid then decomposes to carbon dioxide and water.

In the method of the present invention, formic acid is reacted with hydrogen peroxide which is a strong oxidizing agent. This reaction generates performic acid, which could undergo the decomposition reactions described above. However, in the invention, a two-phase reaction is employed with two solvents which are not miscible. Therefore, there exists an organic phase such as methylene chloride and an aqueous phase. It is most likely that the reaction of formic acid and hydrogen peroxide to generate performic acid occurs in the aqueous phase. However, before the performic acid can significantly decompose to carbon dioxide and water, a certain amount migrates to the organic phase. Conversion of the benzaldehyde to the formate ester, B in the above reaction, then occurs in the organic phase due to the action of performic acid upon the benzaldehyde. In order to make this reaction work, the large excess of both hydrogen peroxide and formic acid previously stated is required to compensate for decomposition of the performic acid.

As additional proof of the importance of performic acid to this method, it has been observed that reaction of a benzaldehyde in methylene chloride with aqueous hydrogen peroxide in the absence of formic acid results in the exclusive formation of the corresponding benzoic acid. This indicates that the agent acting upon the aldehyde is either hydrogen peroxide, to provide acid, or performic acid, to give formate ester.

The invention employs a low-boiling solvent such as methylene chloride (b.p. 40° C.) so that the reaction is quite mild and undesired side-reactions are minimized. Additionally, since the reaction medium is mildly acidic, conditions under which the formate ester is stable, no phenol is prematurely formed. Premature formation of a phenol, in the presence of hydrogen peroxide, would otherwise lead to undesired oxidation of the phenol, and thus reduce the efficiency of the method.

Upon consumption of the benzaldehyde by conversion to formate ester, the synthesis is completed by mild saponification of the formate ester. Saponification is a method for the cleavage of an ester and mechanistically entails hydrolysis by the addition of one molecule of water to one molecule of ester resulting in destruction of the ester with formation of one molecule of the phenol and one molecule of carboxylic acid.

The method of the present invention basically includes:
1.) A two-phase reaction medium with an organic phase and an aqueous phase.
2.) The generation of performic acid in the two-phase system.
3.) The oxidation of a benzaldehyde to a formate ester in the two-phase system.
4.) The use of a large excess of both hydrogen peroxide and formic acid to compensate for the decomposition of performic acid to carbon dioxide and water.

The reaction mixture of aldehyde, hydrogen peroxide, formic acid and organic solvent is mixed to form the two-phase reaction medium and maintained at a temperature of 25° C. to 100° C., preferably 30° C. to 50° C., for a period of time varying between 2 hours and 24 hours, preferably 18 hours to 20 hours. Remaining hydrogen peroxide and formic acid are neutralized by addition of a caustic solution, preferably aqueous sodium hydroxide. However, the caustic solution may be any of the aqueous solutions of the hydroxides of the alkali and alkaline earth metals such as potassium hydroxide or calcium hydroxide. Separation of the organic phase and removal of the organic solvent provides a crude material rich in the formate ester. Dilution of this material with an inert solvent such as methanol, ethanol or tetrahydrofuran, preferably methanol, and mixing with the previous aqueous caustic solution results in saponification of the formate ester. Subsequent acid-base extraction provides for isolation of the phenolic product, C in the above reaction.

The following examples represent preferred embodiments of the present invention. These examples describe particular equipment and methodologies, but other equipment and methodologies can be used. Additionally, other materials can be used as suggested above.

EXAMPLE 1

2,2-Dimethyl-1,3-benzodioxol-4-ol

In a 3 L flask, 51.00 g of 2,2,-dimethylbenzodioxole-4-carboxaldehyde (0.286 mol) was placed. The flask was fitted with a reflux condenser and 1.43 L of methylene chloride was added, followed by 161 mL of 30% aqueous hydrogen peroxide (1.57 mol., 5.5 equivalents), and 71.3 mL of formic acid (1.89 mol., 6.6 equivalents). The two-phase mixture was heated to reflux for 21 hours with stirring.

The mixture was allowed to cool to room temperature, then carefully treated with 1.5 L of 1.5N sodium hydroxide (2.25 mol., 7.9 equivalents) in order to destroy any unreacted hydrogen peroxide, plus begin the saponification of the formate ester. The mixture was stirred for 15 minutes after the addition was complete. The organic layer was removed and concentrated to a residue using a rotary evaporator. The residue was diluted with methanol (1 L) and added to a solution of 1.5N sodium hydroxide. The mixture was stirred at room temperature for 30 minutes, after which analytical measurements demonstrated that the formate had been completely hydrolyzed. The methanol was then removed using a rotary evaporator. The neutral by-products were removed form the aqueous solution by extraction with two 1 L portions of methylene chloride. The combined neutral extracts were dried over anhydrous magnesium sulfate, filtered and concentrated using a rotary evaporator to provide 1.39 g of neutral by-products. The pH of the remaining aqueous solution was then adjusted to 1 or 2 with concentrated hydrochloric acid. The phenolic product was extracted with three 1 L portions of fresh methylene chloride. The combined phenolic extracts were dried over anhydrous magnesium sulfate, filtered and concentrated using a rotary evaporator to provide 41.86 g of the phenolic product, for a 88.1% crude yield. Purification by bulb-to-bulb distillation afforded 38.14 g of the desired product (0.23 mol) for a 80.3% yield. The purity was determined by gas chromatography (GC) to be >99.9% and by high performance liquid chromatography (HPLC) to be 97.5%.

EXAMPLE 2

Sesamol

In a 3 L flask were placed 50.0 g (0.333 mol) of piperonal and 1650 mL of methylene chloride (0.2M). This mixture was vigorously stirred with a magnetic stir bar. To the homogeneous solution was added 84.95 mL of 30% aqueous hydrogen peroxide (0.833 mol., 2.5 equivalents) and 50.25 mL of formic acid (1.332 mol., 4.0 equivalents). The flask was fitted with a reflux condenser and heated to reflux for 18 hours with stirring. The reaction was monitored by thin layer chromatography.

After cooling, equal proportions of both phases were transferred to a 2 L flask leaving 60% of the volume in the 3 L flask. Aqueous sodium hydroxide (1.5N, 2.63 mol., 7.9 equivalents) was added to the 2 L flask (700 mL) and to the 3 L flask (1050 mL). These solutions were stirred for 15 minutes. The organic layers were separated and concentrated to a residue using a rotary evaporator. The residues were combined with their respective aqueous solutions and 467 mL of methanol was added to the 2 L flask and 700 mL was added to the 3 L flask. These solutions were stirred for 30 minutes. Thin layer chromatography indicated the formate ester had been hydrolyzed to form sesamol. The methanol was removed using a rotary evaporator.

The neutral materials were removed from the aqueous solutions by extracting with two 500 mL portions of methylene chloride for each of two equal aliquots of the aqueous solution. The solutions were then adjusted to a pH of 1 to 2 with concentrated hydrochloric acid. The sesamol was extracted with three 500 mL portions of methylene chloride for each of the two aliquots.

The organic solutions containing the neutrals as well as those containing the product sesamol were separately dried over anhydrous magnesium sulfate and filtered into tared roundbottom flasks. The methylene chloride was removed using a rotary evaporator. A total of 2.17 g of neutrals was recovered of which 82.0% was piperonal as determined by GC. A total of 43.27 g of the crude sesamol was obtained (0.313 mol., 94.1% yield).

The sesamol was purified by bulb-to-bulb distillation. A mass of 35.81 g of sesamol was obtained as an off-white solid (0.259 mol., 77.9% yield). The purity was determined by GC (98.7%) as well as HPLC (98.7%).

EXAMPLE 3

2-Methyoxyphenol

In a 500 mL flask were placed 5.0 g (36.7 mmol) of o-anisaldehyde and 184 mL of methylene chloride (0.2M). This mixture was vigorously stirred with a magnetic stir bar. To the homogeneous solution was added 9.37 mL of 30% aqueous hydrogen peroxide (92.0 mmol., 2.5 equivalents) and 5.54 mL of formic acid (14.7 mmol., 4.0 equivalents). The flask was fitted with a reflux condenser and heated to reflux for 22 hours with stirring.

After cooling, 119 mL of 1.5N sodium hydroxide (179 mmol., 4.86 equivalents) was added to the flask. The mixture was stirred for 15 minutes. The organic layer was separated and concentrated to a residue using a rotary evaporator. The residue was combined with the aqueous solution and 79.3 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The guaiacol was extracted with three 100 mL portions of methylene chloride.

The organic solution containing the neutrals as well as the one containing the product were separately dried over anhydrous magnesium sulfate and filtered into tared roundbottom flasks. The methylene chloride was removed using a rotary evaporator. A total of 0.715 g of neutrals was recovered. A total of 4.63 g of the crude guaiacol was obtained (37.3 mmol., 102% yield). The guaiacol was purified utilizing bulb-to-bulb distillation. A mass of 3.44 g of guaiacol as a clear liquid was obtained (27.7 mmol., 75.5% yield). The purity was determined by GC (99.9%) as well as HPLC (>99.9%).

EXAMPLE 4

3-Methoxyphenol

In a 500 mL flask were placed 5.0 g (36.7 mmol) of m-anisaldehyde and 184 mL of methylene chloride (0.2M). This mixture was vigorously stirred with a magnetic stir bar. To the homogeneous solution was added 9.37 mL of 30% aqueous hydrogen peroxide (92.0 mmol., 2.5 equivalents) and 5.54 mL of formic acid (147 mmol., 4.0 equivalents). The flask was fitted with a reflux condenser and heated to reflux for 20 hours with stirring.

After cooling, 119 mL of 1.5N sodium hydroxide (1 79 mmol., 4.86 equivalents) was added to the flask. The mixture was stirred for 15 minutes. The organic layer was separated and concentrated to a residue using a rotary evaporator. The residue was combined with the aqueous solution and 79.3 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 3-methoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.717 g of neutrals was recovered. A total of 4.55 g of the crude 3-methoxyphenol and m-anisic acid was obtained.

The 3-methoxyphenol was purified utilizing bulb-to-bulb distillation. A mass of 0.753 g of 3-methoxyphenol as a clear liquid was obtained (6.07 mmol., 16.5% yield). The purity was determined by GC (96.3%) as well as HPLC (86.4%). The 3.78 g of residue remaining in the flask was m-anisic acid (24.9 mmol., 75.9% yield). The purity was determined by HPLC (99.0%).

EXAMPLE 5

4-Methoxyphenol

In a 500 mL flask were placed 5.0 g (36.7 mmol) of p-anisaldehyde and 184 mL of methylene chloride (0.2M). This mixture was vigorously stirred with a magnetic stir bar. To the homogeneous solution was added 9.37 mL of 30% aqueous hydrogen peroxide (92.0 mmol., 2.5 equivalents) and 5.54 mL of formic acid (147 mmol., 4.0 equivalents). The flask was then fitted with a reflux condenser and heated to reflux for 20.5 hours with stirring.

After cooling, 119 mL of 1.5N sodium hydroxide (179 mmol., 4.86 equivalents) was added to the flask. The mixture was stirred for 15 minutes. The organic layer was separated and concentrated to a residue using a rotary evaporator. The residue was combined with the aqueous solution and 79.3 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 4-methoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.052 g of neutrals was recovered. A total of 4.13 g of the crude 4-methoxyphenol was obtained (33.3 mmol., 90.7% yield).

The 4-methoxyphenol was purified utilizing bulb-to-bulb distillation. A mass of 3.88 g of 4-methoxyphenol as a white crystalline solid was obtained (31.3 mmol., 85.1 % yield). The purity was determined by GC (99.7%) as well as HPLC (99.3%).

EXAMPLE 6

2,3-Dimethoxyphenol

In a 500 mL flask were placed 5.0 g (30.1 mmol) of 2,3-dimethoxybenzaldehyde and 150 mL of methylene chloride (0.2M). This mixture was vigorously stirred with a magnetic stir bar. To the homogeneous solution was added 7.68 mL of 30% aqueous hydrogen peroxide (75.0 mmol., 2.5 equivalents) and 5.54 mL of formic acid (120.0 mmol., 4.0 equivalents). The flask was fitted with a reflux condenser and heated to reflux for 20 hours with stirring.

After cooling, 97.5 mL of 1.5N sodium hydroxide (146 mmol., 4.85 equivalents) was added to the flask. The mixture was stirred for 15 minutes. The organic layer was separated and concentrated to a residue using a rotary evaporator. The residue was combined with the aqueous solution and 65.0 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 2,3-dimethoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.198 g of neutrals was recovered. A total of 4.34 g of the crude 2,3-dimethoxyphenol was obtained (28.1 mmol., 93.5% yield).

The 2,3-dimethoxyphenol was purified utilizing bulb-to-bulb distillation. A mass of 3.49 g of 2,3-dimethoxyphenol as a yellowish liquid was obtained (22.6 mmol., 75.2% yield). The purity was determined by GC (99.9%) as well as HPLC (99.8%).

EXAMPLE 7

2,4-Dimethoxyphenol

In a 500 mL flask were placed 5.0 g (30.1 mmol) of 2,4-dimethoxybenzaldehyde and 150.4 mL of methylene chloride (0.2M). This mixture was vigorously stirred with a magnetic stir bar. To the homogeneous solution was added 7.7 mL of 30% aqueous hydrogen peroxide (75.0 mmol., 2.5 equivalents) and 4.5 mL of formic acid (120.0 mmol., 4.0 equivalents). The flask was fitted with a reflux condenser and heated to reflux for 22 hours with stirring.

After cooling, 97.5 mL of 1.5N sodium hydroxide (146 mmol., 4.86 equivalents) was added to the flask. The mixture was stirred for 15 minutes. The organic layer was separated and concentrated to a residue using a rotary evaporator. The residue was combined with the aqueous solution and 65.0 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 2,4-dimethoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.267 g of neutrals was recovered. A total of 3.52 g of the crude 2,4-dimethoxyphenol was obtained (22.9 mmol., 76.0% yield).

The 2,4-dimethoxyphenol was purified utilizing bulb-to-bulb distillation. A mass of 2.94 g of 2,4-dimethoxyphenol as brown liquid was obtained (19.1 mmol., 63.4% yield). The purity was determined by GC (97.9%) as well as HPLC (>99.9%).

EXAMPLE 8

2,5-Dimethoxyphenol

In a 500 mL flask were placed 5.0 g (30.1 mmol) of 2,5-dimethoxybenzaldehyde and 150 mL of methylene chloride (0.2M). This mixture was vigorously stirred with a magnetic stir bar. To the homogeneous solution was added 7.68 mL of 30% aqueous hydrogen peroxide (75.2 mmol., 2.5 equivalents) and 4.54 mL of formic acid (120.4 mmol., 4.0 equivalents). The flask was fitted with a reflux condenser and heated to reflux for 20 hours with stirring.

After cooling, 97.5 mL of 1.5N sodium hydroxide (146 mmol., 4.86 equivalents) was added to the flask. The mixture was stirred for 15 minutes. The organic layer was separated and concentrated to a residue using a rotary evaporator. The residue was combined with the aqueous solution and 65.0 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 2,5-dimethoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.247 g of neutrals was recovered. A total of 3.91 g of the crude 2,5-dimethoxyphenol was obtained (25.4 mmol., 84.4% yield).

The 2,5-dimethoxyphenol was purified utilizing bulb-to-bulb distillation. A mass of 3.49 g of 2,5-dimethoxyphenol as a brownish liquid was obtained (22.7 mmol., 75.3% yield). The purity was determined by GC (99.8%) as well as HPLC (99.5%).

EXAMPLE 9

3,4-Dimethoxyphenol

In a 500 mL flask were placed 5.0 g (30.1 mmol) of 2,3-dimethoxybenzaldehyde and 151 mL of methylene chloride (0.2M). This mixture was vigorously stirred with a magnetic stir bar. To the homogeneous solution was added 7.68 mL of 30% aqueous hydrogen peroxide (75.0 mmol., 2.5 equivalents) and 5.54 mL of formic acid (120.0 mmol., 4.0 equivalents). The flask was fitted with a reflux condenser and heated to reflux for 20 hours with stirring.

After cooling, 97.5 mL of 1.5N sodium hydroxide (146 mmol., 4.86 equivalents) was added to the flask. The mixture was stirred for 15 minutes. The organic layer was separated and concentrated to a residue using a rotary evaporator. The residue was-combined with the aqueous solution and 65.0 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 3,4-dimethoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.509 g of neutrals was recovered. A total of 4.19 g of the crude 3,4-dimethoxyphenol was obtained (27.2 mmol., 90.3% yield).

The 3,4-dimethoxyphenol was purified utilizing bulb-to-bulb distillation. A mass of 3.43 g of 3,4-dimethoxyphenol as an off-white solid was obtained (22.3 mmol., 74.0% yield). The purity was determined by GC (99.9%) as well as HPLC (98.6%).

EXAMPLE 10

2,3,4-Trimethoxyphenol

In a 500 mL flask were placed 5.0 g (25.5 mmol) of 2,3,4-trimethoxybenzaldehyde and 127 mL of methylene chloride (0.2M). This mixture was vigorously stirred with a magnetic stir bar. To the homogeneous solution was added 6.50 mL of 30% aqueous hydrogen peroxide (64.0 mmol., 2.5 equivalents) and 3.84 mL of formic acid (101 mmol., 4.0 equivalents). The flask was fitted with a reflux condenser and heated to reflux for 20 hours with stirring.

After cooling, 82.4 mL of 1.5N sodium hydroxide (124 mmol., 4.85 equivalents) was added to the flask. The mixture was stirred for 15 minutes. The organic layer was separated and concentrated to a residue using a rotary evaporator. The residue was combined with the aqueous solution and 54.9 mL of methanol was added. The solution was stirred for 30 minutes. The methanol was removed using a rotary evaporator.

The neutral materials were removed from the aqueous residue by extracting with two a 100 mL portions of methylene chloride. The solution was adjusted to a pH of 1 to 2 with concentrated hydrochloric acid. The 2,3,4-trimethoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.0148 g of neutrals was recovered. A total of 4.25 g of the crude 2,3,4-trimethoxyphenol was obtained (23.1 mmol., 90.6% yield).

The 2,3,4-trimethoxyphenol was purified utilizing bulb-to-bulb distillation. A mass of 3.85 g of 2,3,4-trimethoxyphenol as an off-white solid was obtained (20.9 mmol., 82.0% yield). The purity was determined by GC (99.9%) as well as HPLC (>99.9%).

EXAMPLE 11

2,4,5-Trimethoxyphenol

In a 500 mL flask were placed 5.0 g (25.5 mmol) of 2,4,5-trimethoxybenzaldehyde and 127 mL of methylene chloride (0.2M). This mixture was vigorously stirred with a magnetic stir bar. To the homogeneous solution was added 6.50 mL of 30% aqueous hydrogen peroxide (64.0 mmol., 2.5 equivalents) and 3.84 mL of formic acid (101.0 mmol., 4.0 equivalents). The flask was fitted with a reflux condenser and heated to reflux for 20 hours with stirring.

After cooling, 82.4 mL of 1.5N sodium hydroxide (124 mmol., 4.85 equivalents) was added to the flask. The mixture was stirred for 15 minutes. The organic layer was separated and concentrated to a residue using a rotary evaporator. The residue was combined with the aqueous solution and 54.9 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 2,4,5-trimethoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.121 g of neutrals was recovered. A total of 3.26 g of the crude 2,4,5-trimethoxyphenol was obtained (17.7 mmol., 69.4% yield).

The 2,4,5-trimethoxyphenol was purified utilizing bulb-to-bulb distillation. A mass of 2.23 g of 2,4,5-trimethoxyphenol as an off-white solid was obtained (12.1 mmol., 47.4% yield). The purity was determined by GC (99.5%) as well as HPLC (>99.9%).

EXAMPLE 12

2,4,6-Trimethoxyphenol

In a 500 mL flask were placed 5.0 g (25.5 mmol) of 2,4,6-trimethoxybenzaldehyde and 127 mL of methylene chloride (0.2M). This mixture was vigorously stirred with a magnetic stir bar. To the homogeneous solution was added 6.50 mL of 30% aqueous hydrogen peroxide (64.0 mmol., 2.5 equivalents) and 3.84 mL of formic acid (101.0 mmol., 4.0 equivalents). The flask was fitted with a reflux condenser and heated to reflux for 18 hours with stirring.

After cooling, 82.4 mL of 1.5N sodium hydroxide (124 mmol., 4.85 equivalents) was added to the flask. The mixture was stirred for 15 minutes. The organic layer was separated and concentrated to a residue using a rotary evaporator. The residue was combined with the aqueous solution and 54.9 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 2,4,6-trimethoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.547 g of neutrals was recovered. A total of 2.72 g of the crude 2,4,6-trimethoxyphenol and 2,4,6trimethoxybenzoic acid was obtained.

The 2,4,6-trimethoxyphenol was purified utilizing bulb-to-bulb distillation. A mass of 0.0974 g of 2,4,6-trimethoxyphenol as brown liquid was obtained (0.529 mmol., 2.08% yield). The purity was determined by GC (83.1 %) as well as HPLC (92.0%). The 1.83 g which remained in the flask was determined to be 2,4,6-trimethoxybenzoic acid (46% by HPLC).

EXAMPLE 13

3,4,5-Trimethoxyphenol

In a 500 mL flask were placed 5.0 g (25.5 mmol) of 3,4,5-trimethoxybenzaldehyde and 127 mL of methylene chloride (0.2M). This mixture was vigorously stirred with a magnetic stir bar. To the homogeneous solution was added 6.50 mL of 30% aqueous hydrogen peroxide (64.0 mmol., 2.5 equivalents) and 3.84 mL of formic acid (101.0 mmol., 4.0 equivalents). The flask was fitted with a reflux condenser and heated to reflux for 18 hours with stirring.

After cooling, 82.4 mL of 1.5N sodium hydroxide (124 mmol., 4.85 equivalents) was added to the flask. The mixture was stirred for 15 minutes. The organic layer was separated and concentrated to a residue using a rotary evaporator. The residue was combined with the aqueous solution and 54.9 mL of methanol was added. The solution was stirred for 30 minutes. The methanol was removed using a rotary evaporator.

The neutral materials were removed from the aqueous residue by extracting with two 100 mL portions of methylene chloride. The solution was adjusted to a pH of 1 to 2 with concentrated hydrochloric acid. The 3,4,5-trimethoxyphenol was extracted with three 100 mL portions of methylene chloride.

The organic solution containing the neutrals as well as the one containing the product were separately dried over anhydrous magnesium sulfate and filtered into tared round-bottom flasks. The methylene chloride was removed using a rotary evaporator. A total of 0.408 g of neutrals was recovered. A total of 2.59 g of the crude 3,4,5-trimethoxyphenol and 3,4,5trimethoxybenzoic acid was obtained.

The 3,4,5-trimethoxyphenol was purified utilizing bulb-to-bulb distillation. A mass of 0.0693 g of 3,4,5-trimethoxyphenol as a brown liquid was obtained (0.376 mmol., 1.48% yield). The purity was determined by GC (22.71%) as well as HPLC (15.4%). The 2.31 g (42.8% yield) of 3,4,5-trimethoxybenzoic acid remaining in the flask was determined to be 91.7% pure by GC and 94.2% pure by HPLC.

The advantages of the present invention as compared to the prior art are that: 1) the reagents are inexpensive; 2) oxidation of the benzaldehyde to the corresponding benzoic acid is negligible; 3) benzaldehydes may be used as the substrates for the reaction rather than acetophenones; 4) a sacrificial aldehyde is not required; and 5) the process is specific with regard to the phenolic isomer that is produced. The method has been demonstrated to be particularly useful for the conversion of piperonal to sesamol but many other applications are possible. For a listing of the utility of the products of the present invention, reference is made to British Patent 1,220,056.

Many modifications of the process, conditions and substrates described above may be made by those skilled in the art to achieve a wide variance of results to suit specific needs or objectives without departing from the scope of the invention described and claimed herein. Specifically, although examples have been given involving certain concentrations of materials, much higher concentrations may be employed resulting in reduced reaction times. Also, changing the relative proportions of solvents is within the scope of the invention.

We claim:

1. A method for the production of alkoxy- and aryloxy-phenols comprising the steps of:
   a. providing a two-phase mixture of the corresponding alkoxy- or aryloxy-benzaldehyde in an organic solvent phase and from 3 to 7 molar equivalents formic acid and from 2 to 6 molar equivalents hydrogen peroxide in an aqueous solvent phase, said organic solvent phase being immiscible in said aqueous solvent phase and being a solvent for said benzaldehyde and for performic acid and being non-reactive with said hydrogen peroxide and performic acid;

b. subjecting said two-phase mixture to stirring and reaction conditions whereby said formic acid and said hydrogen peroxide react in said aqueous solvent phase to form performic acid and said performic acid and said benzaldehyde react in said organic solvent phase to form the corresponding alkoxy- or aryloxy- formate ester; and c. saponifying said formate ester to produce the corresponding alkoxy- or aryloxy- phenol.

2. A method as recited in claim 1 wherein said step of saponifying comprises reaction with sodium hydroxide.

3. A method as recited in claim 1 wherein said organic solvent phase comprises a chlorinated solvent.

4. A method as recited in claim 3 wherein said chlorinated solvent is selected from the group consisting of dichloromethane, dichloroethane, chloroform and carbon tetrachloride.

5. A method as recited in claim 1 wherein said reaction conditions include heating said two-phase mixture to reflux.

6. A method as recited in claim 1 wherein said step of saponifying includes neutralizing any unreacted hydrogen peroxide and formic acid by reaction with a caustic solution.

* * * * *